US007332184B2

(12) United States Patent
Vanner et al.

(10) Patent No.: US 7,332,184 B2
(45) Date of Patent: Feb. 19, 2008

(54) COLONIC CLEANSING COMPOSITION AND METHOD

(75) Inventors: Stephen J. Vanner, Kingston (CA); William T. Depew, Kingston (CA); Robert L. Barclay, Rockford, IL (US)

(73) Assignee: Queen's University at Kingston, Kingston, Ontario (CA)

( * ) Notice: Subject to any disclaimer, the term of this patent is extended or adjusted under 35 U.S.C. 154(b) by 0 days.

(21) Appl. No.: 10/401,505

(22) Filed: Mar. 28, 2003

(65) Prior Publication Data

US 2004/0192614 A1 Sep. 30, 2004

(51) Int. Cl.
*A61K 33/14* (2006.01)
*A61K 33/42* (2006.01)
*A61K 31/7004* (2006.01)
*A61K 31/7016* (2006.01)
*A61P 1/00* (2006.01)
*A61P 3/12* (2006.01)

(52) U.S. Cl. ............... 424/606; 424/601; 424/679; 424/680; 424/722; 514/23; 514/53; 514/892; 514/974

(58) Field of Classification Search ............... 424/606, 424/677, 679–680; 514/23, 892
See application file for complete search history.

(56) References Cited

U.S. PATENT DOCUMENTS 6,866,873 B2 * 3/2005 Stern .................. 424/725
2005/0271749 A1 * 12/2005 Borody et al. ........... 424/722

OTHER PUBLICATIONS

Tjandra, J., et al., "Carbohydrate-Electrolyte (E-Lyte®) Solution Enhances Bowel Preparation With Oral Fleet® Phospho-soda®", 2004, Dis Colon Rectum, 47, pp. 1181-1186.
Afridi et al., "Prospective, Randomized Trial Comparing a New Sodium Phosphate-Bisacodyl Regimen with Conventional PEG-ES Lavage for Outpatient Colonoscopy Preparation," Gastrointest. Endosc., 1995, pp. 485-489, vol. 41.
Arezzo, "Prospective Randomized Trial Comparing Bowel Cleaning Preparations for Colonoscopy," Surgical Laparoscopy & Percutaneous Techniques, 2000, pp. 215-217, vol. 10.
Aronchick et al., "A Novel Tableted Purgative for Colonoscopic Preparation: Efficacy and Safety Comparisons with Colyte and Fleet Phospho-Soda," Gastrointest Endosc., 2000, pp. 346-352, vol. 52.
Avery et al., "Oral Therapy for Acute Diarrhea: The Underused Simple Solution," N. Engl. J. Med., 1990, pp. 891-894, vol. 13.
Barclay et al., "Carbohydrate-Electrolyte Rehydration Protects Against Intravascular Volume Contraction During Colonic Cleansing with Orally Administered Sodium Phosphate," Gastrointest. Endosc., 2002, pp. 633-638, vol. 56.
Bawani et al., "A Single Blinded, Prospectively Randomized Comparison of Oral Phosphosoda (OP) with Polyethylene Glycol Based Solution (PG) as a Colonic Lavage for Colonoscopy," Am. J. Gastroent., 1991, p. 1350, vol. 86, Abstract 239.
Bawani et al., "A Single Blind Control Study of Fleet Oral Phosphosoda Laxative and Magnesium Citrate for Colonoscopy Preparation," Presented at AJG, 1996, p. 1964, vol. 91, Abstract 316.
Berkelhammer et al., "Low-Volume Oral Colonoscopy Bowel Preparation: Sodium Phosphate and Magnesium Citrate," Gastrointest. Endoscopy, 2002, pp. 89-94, vol. 56.
Bujanda et al., "Tolerance and Colon Cleansing with Two Preparations. Polyethylene Glycol Versus Sodium Phosphate," Gastroenterologia Y. Hepatologia, 2001, pp. 9-12, vol. 24.
Chaleoykitti, "Comparative Study Between Polyethylene Glycol and Sodium Phosphat Solution in Elective Colorectal Surgery," J. Med. Assoc. Thai, 2002, pp. 92-96, vol. 85.
Chan et al., "Use or Oral Sodium Phosphate Colonic Lavage Solution by Canadian Colonoscopists: Pitfalls and Complications," Can J. Gastroenterol., 1997, pp. 334-338, vol. 11.
Chia et al., "Role of Oral Sodium Phosphate and Its Effectiveness in Large Bowel Preparation for Out-Patient Colonoscopy," J.R. Coll. Surg. Edinb., 1995, pp. 374-376, vol. 40.
Chilton et al., "A Blinded, Randomized Comparison of a Novel, Low-Dose, Triple Regimen with Fleet Phospho-soda: A Study of Colon Cleanliness, Speed and Success of Colonoscopy," Endoscopy, 2000, pp. 37-41, vol. 32.
Clarkston et al., "Oral Sodium Phosphate Versus Sulfate-Free Polyethylene Glycol Electrolyte Lavage Solution in Outpatient Preparation for Colonoscopy: A Prospective Comparison," Gastrointest. Endosc., 1996, pp. 42-48, vol. 43.
Cohen et al., "Prospective, Randomized, Endoscopic-Blinded Trial Comparing Precolonoscopy Bowel Cleansing Methods," Dis. Colon Rectum, 1994, pp. 689-696, vol. 37.
Da Silva et al., "Colonoscopy Preparation in Children: Safety, Efficacy, and Tolerance of High- Versus Low-Volume Cleansing Methods," J. Pediatr. Gastroent. Nutr., 1997, pp. 33-37, vol. 24.
Del Piano et al., "Comparison of 3 Methods of Preparation for Colonoscopy," Minerva Gastroenterol. Dietol, 1993, pp. 89-92, vol. 39.
Fernandez et al., "Characterization of the Safety, Effectiveness and Use of Oral Sodium Phosphate," Rev. Esp. Enferm. Dig, 2001, pp. 220-225, vol. 93.
Frommer, "Cleansing Ability and Tolerance of Three Bowel Preparation for Colonoscopy," Dis. Colon Rectum, 1997, pp. 100-104, vol. 40.
Golub et al., "Colonoscopic Bowel Preparations—Which One?," Dis. Colon. Rectum., 1995, pp. 594-598, vol. 38.
Greenleaf et al., "Plasma Volume Expansion with Oral Fluids in Hypohydrated Men at Rest and During Exercise," Aviat Space Environ. Med., 1998, pp. 837-844, vol. 69.
Gremse et al., "Comparison of Oral Sodium Phosphate to Polyethylene Glycol-Based Solution for Bowel Preparation for Colonoscopy in Children," J. Ped. Gast. And Nutrition, 1996, pp. 586-590, vol. 23.
Habr-Gama, "Bowel Preparation for Colonscopy: Comparison of Mannitol and Sodium Phosphate: Results of a Prospective Randomized Study," Rev. Hosp. Clin. Fac. Med. S. Paulo, 1999, pp. 187-192, vol. 54.

(Continued)

*Primary Examiner*—John Pak
(74) *Attorney, Agent, or Firm*—Evan Law Group LLC

(57) ABSTRACT

A colonic cleansing kit comprises an osmotic colonic evacuant, and an oral rehydration mixture. The oral rehydration mixture comprises sugar, and salt. The sugar comprises a glucose containing saccharide, and the salt comprises sodium.

17 Claims, 1 Drawing Sheet

OTHER PUBLICATIONS

Handelsman et al., "Experience with Ambulatory Preoperative Bowel Preparation at The Johns Hopkins Hospital," Arch. Surg., 1993, pp. 441-444, vol. 128.

Haroon et al., "A Randomized Clinical Trial Comparing Oral Sodium Phosphate (NaP) with Standard Polyethylene Glucol-Based Lavage Solution (Colyte) in the Preparation of Patients for Colonoscopy," American Gastroenterological Assoc., 1992, Abstract No. 2112.

Henderson et al., "Single-Day, Divided-Dose Oral Sodium Phosphate Laxative Versus Intestinal Lavage as Preparation for Colonoscopy: Efficacy and Patient Tolerance," Gastrointest. Endoscopy, 1995, pp. 238-243, vol. 42.

Hookey et al., "The Safety Profile of Oral Sodium Phosphate Regimen for Colonoscopy Cleansing: Lack of Clinically Significant Hypocalcemia or Hypovolemia," Am. J. Gastroenter., 1995, pp. 104-107, vol. 90.

Huynh et al., "Safety Profile of 5-H Oral Sodium Phosphate Regimen for Colonoscopy Cleansing: Lack of Clinically Significant Hypocalcemia or Hypovolemia," Am. J. Gastroenterol., 1995, pp. 104-107, vol. 90.

Johnson et al., "Dehydration and Orthostatic Vital Signs in Women with Hyperemesis Gravidarum," Acad. Emerg. Med., 1995, pp. 692-697, vol. 2.

Kim et al., "Patient Compliance and Satisfaction with Oral Bowel Preparation for Outpatient Colonoscopy: A Prospective, Randomized, Blinded Trial," Dis. Colon Rectum, 1997, vol. 40, Abstract No. P48.

Klein et al., "Enteral and Parenteral Nutrition," Sleisenger and Fordtran's Gastrointestinal and Liver Disease, 1998, pp. 254-277.

Kolts et al., "A Comparison of the Effectiveness and Patient Tolerance of Oral Sodium Phosphate, Castor Oil, and Standard Electrolyte Lavage for Colonoscopy or Sigmoidoscopy Preparation," Am. J. Gastroenterol., 1993, pp. 1218-1223, vol. 88.

Kuchel et al., "Cardiovascular Responses to Phlebotomy and Sitting in Middle-Aged and Elderly Subjects," Arch. Int. Med., 1992, pp. 366-370, vol. 152.

Lapalus et al., "Prospective Randomized Single-Blind Trial to Compare Oral Sodium Phosphate and Polyethylene Glycol for Colonoscopy Preparation," Gastroenterol. Clin. Biol., 2001, pp. 29-34, vol. 25.

Lee et al., "A Prospective Randomised Study Comparing Polyethylene Glycol and Sodium Phosphate Bowel Cleansing Solutions for Colonoscopy," The Ulster Medical Journal, 1999, pp. 68-72, vol. 68.

McGee, "Physical Examination of Venous Pressure: A Critical Review," Am. Heart H., 1998, pp. 10-18, vol. 136.

Macari et al., "Effect of Different Bowel Preparations on Residual Fluid at CT Colonography," Radiology, 2001, pp. 274-277, vol. 218.

MacLeod et al., "A Comparison of Fleet Phospho-Soda with Picolax in the Preparation of the Colon for Double Contrast Barium Enema," Clinical Radiology, 1998, pp. 612-614, vol. 53.

Marshall et al., "Short Report: Prospective, Randomized Trial Comparing a Single Dose Sodium Phosphate Regimen with PEG-Electrolyte Lavage for Colonoscopy Preparation," Aliment Pharmacol. Ther., 1993, pp. 679-682, vol. 7.

Marshall et al., "Prospective, Randomized Trial Comparing Sodium Phosphate Solution with Polyethylene Glycol-Electrolyte Lavage for Colonoscopy Preparation," Gastrointest. Endosc., 1993, pp. 631-634, vol. 39.

Martinek et al., "Cisapride Does Not Improve Precolonoscopy Bowel Preparation with Either Sodium Phosphate or Polyethylene Glycol Electrolyte Lavage," Gastrointest. Endoscopy, 2001, pp. 180-185, vol. 54.

Maughan et al., "Post-Exercise Rehydration in Man: Effects of Electrolyte Addition to Ingested Fluids," Eur. J. Appl. Physiol. Occoup. Physiol., 1994, pp. 209-225, vol. 69.

O'Donovan et al., "A Prospective Blinded Randomized Trial Comparing Oral Sodium Phosphate and Polyethylene Glycol Solutions for Bowel Preparation Prior to Barium Enema," Clin. Radiology, 1997, pp. 791-793, vol. 52.

Oliveria et al., "Mechanical Bowel Preparation for Elective Colorectal Surgery, A Prospective, Randomized, Surgeon-Blinded Trial Comparing Sodium Phosphate and Polyethylene Glycol-Based Oral Lavage Solutions," Dis. Colon Rectum, 1997, pp. 585-590, vol. 40.

Poon et al., "Two Liters of Polyethylene Glycol-Electrolyte Lavage Solution Versus Sodium Phosphate as Bowel Cleansing Regimen for Colonoscopy: A Prospective Randomized Controlled Trial," Endoscopy, 2002, pp. 560-563, vol. 34.

Rex et al., "Impact of Bowel Preparation on Efficacy and Cost of Colonoscopy," Am. J. Gastroenterology, 2002, pp. 1696-2000, vol. 97.

Shaoul et al., "Symptoms of Hyperphosphatemia, Hypocalcemia, and Hypomagnesemia in an Adolescent After the Oral Administration of Sodium Phosphate in Preparation for a Colonoscopy," Gastrointest. Endosc., 2001, pp. 650-652, vol. 53.

Sudduth et al., "The Effectiveness of Simethicone in Improving Visibility During Colonoscopy When Given With a Sodium Phosphate Solution: A Double-Blind Randomized Study," Gastrointest. Endoscopy, 1995, pp. 413-415, vol. 42.

Thomson et al., "Bowel Preparation for Colonoscopy: A Randomized Prospective Trial Comparing Sodium Phosphate and Polyethylene Glycol in a Predominantly Elderly Population," J. Gast. and Hepatology, 1996, pp. 103-107, vol. 11.

Unal et al., "A Randomized Prospective Trial Comparing 45 and 90-ML Oral Sodium Phosphate with X-Prep in the Preparation of Patients for Colonoscopy," Acta. Gastroenterol. Belg., 1998, pp. 281-284, vol. 61.

Vanner et al., "A Randomized Prospective Trial Comparing Oral Sodium Phosphate with Standard Polyethylene Glycol-Based Lavage Solution (Golytely) in the Preparation of Patients for Colonoscopy," Am. J. Gastroenterol., 1990, pp. 422-427, vol. 85.

Wolff et al., "A New Bowel Preparation for Elective Colon and Rectal Surgery. A Prospective, Randomized Clinical Trial," Arch. Surg., 1988, pp. 895-900, vol. 123.

Yoshioka et al., "Randomized Trial of Oral Sodium Phosphate (Picolax) for Elective Colorectal Surgery and Colonoscopy," Dig. Surg., 2000, pp. 66-70, vol. 17.

Young et al., "Oral Sodium Phosphate Solution is a Superior Colonoscopy Preparation to Polyethylene Glycol with Bisacodyl," Dis. Colon Rectum, 2000, pp. 1568-1571, vol. 43.

Canard, J., et al., "Fleet® Phospho Soda: for Greater Acceptability of the Colonic Preparation Before Colonoscopy. Randomized Comparative Single Blind Study Versus Polyethylene Glycol." Acta. Endoscopica, 2001, pp. 703-708, vol. 31. Translation of the Canard, J., et al reference.

Oliveira, L.., et al., "Mechanical Bowel Preparation With Oral Sodium Phosphate Solution For Colonoscopy. A New Small Volume Solution Compared To The Traditional Mannitol.", Revista do Colegio Brasileiro de Cirurgioes, 1999, pp. 353-358, vol. 26. Translation of the Oliveira, L.., et al reference.

* cited by examiner

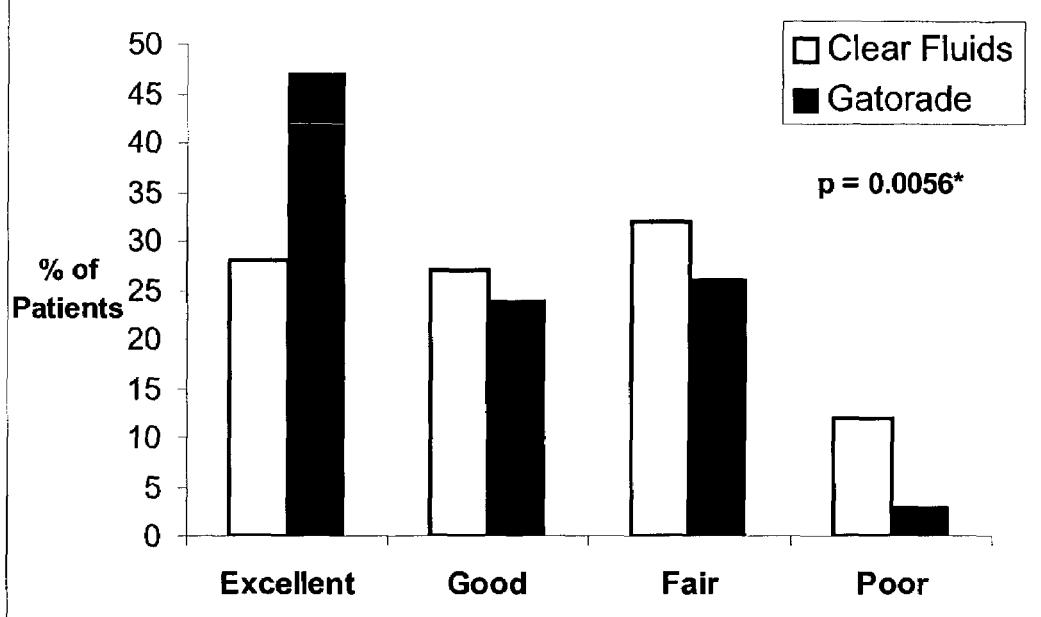

COLONIC CLEANSING COMPOSITION AND METHOD

BACKGROUND

Oral sodium phosphate (NaP), a small volume hypertonic solution of sodium phosphate salts, has emerged as a favorable alternative to large volume polyethylene glycol (PEG)-electrolyte solutions for rapid colonic cleansing prior to colonoscopy. Randomized controlled trials[1-4] have demonstrated equivalent efficacy and superior tolerability of NaP compared to PEG-electrolyte formulations. Consequently, it has become widely used and increasingly is considered the agent of choice for colonic purgation.[5]

With the growing demand for colonoscopy, the importance of optimizing the safety of this procedure becomes increasingly relevant. Although NaP is safe in most patients, its osmotic action has raised concerns about intravascular volume contraction.[7] Previous studies in which hemodynamic variables were measured during oral NaP-based colonic preparation showed evidence of plasma hypovolemia in between 7 to 30% of patients.[1,7] The recent report in a young healthy patient of severe NaP-induced hyperphosphatemia, hypocalcemia and hypomagnesemia,[17] attributed primarily to inadequate fluid consumption, underscores the importance of optimizing plasma volume status during NaP treatment.

BRIEF SUMMARY

In a first aspect, the present invention is a colonic cleansing kit, comprising an osmotic colonic evacuant, and an oral rehydration mixture. The oral rehydration mixture comprises sugar, and salt. The sugar comprises a glucose containing saccharide, and the salt comprises sodium.

In a second aspect, the present invention is a method of colonic. cleansing, comprising orally administering an osmotic colonic evacuant; and orally administering an oral rehydration solution. The oral rehydration solution comprises sugar, salt, and water. The sugar comprises a glucose containing saccharide, the salt comprises sodium, and at least 50% of all fluids orally administered from 4 hours before to 24 hours after orally administering the osmotic colonic evacuant are the oral rehydration solution.

BRIEF DESCRIPTION OF THE DRAWING

FIG. 1 shows the quality of colonic preparation.

DETAILED DESCRIPTION

Oral rehydration has been shown to counteract the intravascular volume contraction associated with acute infectious diarrhea.[8] It was hypothesized that it would similarly attenuate the iatrogenic hypovolemia induced by NaP. Thus, a prospective randomized study compared the effects of an oral rehydration solution with regular clear fluids in patients undergoing oral NaP preparation for colonoscopy. It was discovered that not only does the oral rehydration solution attenuate the hypovolemia, but also results in superior colonic cleansing. The present invention makes use of this discovery.

This study[18] has compiled the largest collection of hemodynamic safety data for patients receiving oral NaP preparation for colonoscopy. Our major finding is that intravascular volume contraction resulting from oral NaP colonic cleansing can be decreased significantly by the ingestion of a readily available, inexpensive oral rehydration solution, for example GATORADE® (the oral rehydration solution used in this study). Although the mean clinical hemodynamic changes secondary to NaP were associated with few reported symptoms of hypovolemia, several subjects had large changes in orthostatic vitals compatible with significant volume contraction. Furthermore, the hemodynamic changes induced by NaP are similar in magnitude to those observed in other acute hypovolemic states, such as hyperemesis gravidarum[12] and phlebotomy in middle-aged and elderly blood donors.[13] Even in the absence of symptoms, acute hypovolemia could increase the risk of end organ hypoperfusional injuries such as syncope, acute tubular necrosis and myocardial ischemia, especially in patients with additional risk factors for such conditions.

A relatively large volume (3.8 L) of supplemental fluid was selected for this study in an attempt to maximize the effects of the oral rehydration solution on plasma volume restoration. Patients designated to drink the oral rehydration solution are indicate by "G" or as "the G group", while those designated to drink clear fluids are designated as "CF" or as "the CF group". Although a greater proportion of subjects in the G group felt that the prescribed fluid volume was too large, the tolerance of the overall bowel preparation was similar between G and CF subjects. Furthermore, the mean fluid volume ingested by G subjects was only slightly larger (difference of 0.43 L) than that reported by CF subjects. This suggests that factors besides volume may have contributed to the adverse perception of G subjects, such as the lack of choice of alternative fluids and the impression of having to ingest a large volume of fluid rather than that of drinking ad libitum over the preparation period. In the present study, the fact that both groups of patients ingested comparable mean volumes of fluid during the preparation period suggests that the composition of the oral rehydration solution was more important than the actual fluid volume in mediating the beneficial effects on plasma volume.

Generally the osmotic colonic evacuant is a composition which causes fluid to be drawn into the intestines and retained, for example a phosphate based laxative, such as sodium dihydrogen phosphate, disodium hydrogen phosphate, sodium biphosphate, sodium acid pyrophosphate, or mixtures thereof; a sulfate based laxative such as sodium picosulfate, sodium sulfate, magnesium sulfate or mixtures thereof; magnesium compounds; and non-absorbable carbohydrates, such as lactulose and L-glucose. Typically the colonic evacuant is a mixture of sodium dihydrogen phosphate and disodium hydrogen phosphate.

The osmotic colonic evacuant may be in solid or liquid form, for example as powder, tablets, capsules, or concentrated liquid. It may be formulated with excipients and/or additives, for example flavoring agents and coloring agents, or even mixed with food.

Oral rehydration mixtures contain sugar and salt; correspondingly, oral rehydration solutions contain sugar, salt and water. The salt contains sodium, and the sugar contains a glucose containing saccharide; the term "glucose containing saccharide" means either glucose, or a saccharide that can be hydrolyzed to form a composition containing glucose. These may also contain a variety of excipients and/or additives, for example flavoring agents, coloring agents, carbonation, viscosity modifiers, preservatives, etc.

Oral rehydration solutions preferably contain from 0.1-15% (w/v) of sugar, more preferably from 1-10% (w/v) sugar, most preferably from 5-7% (w/v) sugar. Preferably, oral rehydration solutions contain from 0.1-200 mmol/L of salt, more preferably from 2-100 mmol/L salt, most preferably from 10-30 mmol/L salt. Oral rehydration mixtures preferably contain salt and sugar in the same proportions as oral rehydration solutions: a ratio of sugar: salt of preferably 0.1-15 g:0.1-200 mmol, more preferably 1-10 g:2-100 mmol, most preferably 5-7 g:10-30 mmol.

Preferably, the oral rehydration solutions are orally adminstered, at least in part after oral adminstration of the osmotic colonic evacuant, and before colonic cleansing caused by the osmotic colonic evacuant is complete. However, it is still expected to be effective if oral administration of the oral rehydration solution is within a few hours prior to oral administration of the osmotic colonic evacuant. At least 50% of all fluids orally administered from 4 hours before to 24 after oral administration of the osmotic colonic evacuant should be an oral rehydration solution, preferably at least 75%, more preferably at least 90%. The term "orally administered" includes, for example, drinking, swallowing one or more pills, eating, etc.

The present invention may be supplied as a kit, containing the osmotic colonic evacuant together with an oral rehydration mixture. The oral rehydration mixture may be supplied in dry form, to which water may be added to form an oral rehydration solution prior to oral administration. The kit may contain two or more containers, packs, or dispensers together with instructions for preparation and administration. Preferably, the kit contains two doses of osmotic colonic evacuant, preferably each in a separate container, and the oral rehydration mixture or solution in one or more additional containers.

The compositions included in the kit may be supplied in containers of any sort such that the life of the different components are preserved, and are not adsorbed or altered by the materials of the container. For example, suitable containers include simple bottles that may be fabricated from glass, organic polymers, such as polycarbonate, polystyrene, etc., ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components to mix. Removable membranes may be glass, plastic, rubber, etc.

Kits may also be supplied with instructional materials. Instructions may be printed on paper or other substrates, and/or may be supplied as an electronic-readable medium, such as a floppy disc, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

The term "flavoring agent" means a natural or artificial compound, or some combination of these, used to impart a pleasant flavor and/or odor to a preparation. Examples include anise oil, cinnamon oil, vanilla, vanillin, cocoa, chocolate, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citric acid; citrus oils such as lemon, orange, lime and grapefruit oils; and fruit essences, including apple, pear, peach, berry, wildberry, date, blueberry, kiwi, strawberry, raspberry, cherry, plum, pineapple, and apricot.

The term "coloring agent" means a compound used to impart color to solid or liquid preparations. Such compounds include, for example FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide. Coloring agents can also include pigments, dyes, tints, titanium dioxide, natural coloring agents such as grape skin extract, beet red powder, beta carotene, annato, carmine, turmeric, and paprika.

The term "salt" means one or more ionic compounds. Examples include sodium chloride, potassium sulfate, and magnesium chloride. Preferably, the salt contains sodium, potassium, and/or magnesium, more preferably the salt contains sodium. Preferably, the salt contains chloride, phosphate and/or citrate. Preferably, the salt has a solubility in water at room temperature of at least one gram per liter.

The sugar means one or more naturally occurring saccharides that has a water solubility of at least one gram per liter. Preferably, the sugar contains mono- and/or di-saccharides. Preferably, the sugar contains glucose, sucrose, galactose, fructose, lactose and/or maltose. More preferably, the sugar contains a glucose containing saccharide. As used herein, reference to any saccharide by a single name also includes all forms of that saccharide which may be in equilibrium with the specific saccharide named, in aqueous solution at room temperature; for example "glucose" includes glucose and all 5- and 6-membered cyclic hemiacetals in equilibrium with glucose in aqueous solution at room temperature.

The therapeutic value of an oral rehydration solution that contains carbohydrates and electrolytes is well established.[8] Glucose enhances sodium absorption by stimulating the cotransporter present in the brush border of intestinal epithelium, leading to passive uptake of water.[14] This mechanism accounts for the success of oral rehydration solutions in the treatment of acute infectious diarrhea, a condition typically characterized by enhanced enteric secretion without impairment of absorptive capacity. Furthermore, hypohydration induced by exercise or changes in altitude can be corrected using an oral rehydration solution, whereas administration of an identical volume of water is ineffective at restoring plasma volume.[15,16]

Although the oral rehydration solution resulted in an important reduction in intravascular volume contraction, it had no demonstrable effect on the hyperphosphatemia resulting from NaP ingestion. Nearly all patients were hyperphosphatemic on the morning after ingestion of NaP, as previously described.[1,7] Some patients had a corresponding drop in serum calcium, but this did not differ significantly between groups. The lowest absolute levels of calcium were observed in the CF group. Although these changes rarely fall within the range that is clinically important,[7] they highlight the lower therapeutic index of NaP and the importance of physicians prescribing the recommended dose to the appropriate patient population.

In summary, this study demonstrates that rehydration with an oral rehydration solution significantly decreases intravascular volume contraction induced by NaP, resulting in a safer procedure for patients. Furthermore, it results in an overall improved degree of colonic cleansing and is well tolerated by patients.

EXAMPLE

Patients and Methods

The study was prospective, randomized, controlled and single-blinded, such that the investigators were unaware of the assigned treatment group of subjects. Patients gave informed written consent prior to enrollment and the study was approved by the Queen's University human ethics committee. Patients with congestive heart failure, renal insufficiency (C>120 umol/L), ascites, or suspected bowel obstruction were excluded. Consecutive adult (age≧18) outpatients who were scheduled to undergo outpatient colonoscopy were randomized (using a list of computer-generated random numbers, each contained in opaque envelopes) to either oral NaP plus ingestion of regular clear fluids during the preparation period (CF group) vs. oral NaP plus ingestion of an oral rehydration solution (GATORADE®, QUAKER OATS Co. of Canada, Peterborough, Ontario) during the preparation period (G group). GATORADE® is an over-the-counter sports drink that contains a 6 % (w/v) mixture of simple carbohydrates (sucrose, glucose, fructose) and small concentrations of sodium (20 mmol/L) and potassium (3 mmol/L). Subjects in the G group were given two 1.9 liter bottles of lemon-lime flavor G and were asked to drink as much of this solution as tolerated from 5 PM the night before the procedure until the morning of the procedure, and to avoid ingesting other fluids. Subjects in the CF group were asked to drink a comparable volume (i.e. ten 8-ounce glasses=3.75 L) of regular fluids (e.g. water, juices, carbonated beverages) but were to refrain from ingesting commercial sports drinks. All other instructions were identical for the two groups and were outlined in written form in a standard pre-colonoscopy information booklet provided to subjects at the initial clinic visit. All subjects maintained a fluid only diet for 24 hours prior to colonoscopy and ingested one bottle (45 cc) of oral NaP (FLEET® PHOSPHO-SODA®, C.B. FLEET Co., Lynchburg, Va.) at 5 PM the night before the procedure and a second bottle at 10 PM. Investigator blinding was maintained by a study nurse and through repeated instructions to patients not to divulge their treatment assignment to attending endoscopy unit personnel.

Hemodynamic and Biochemical Data

Clinical hemodynamic measurements and biochemistry were obtained at enrollment and on the morning of colonoscopy. Hemodynamic data included patient weight, height of jugular venous pressure (JVP) and orthostatic pulse and blood pressure. To ensure consistency in recording methods, one physician obtained all measurements using standardized methods: vitals with patient supine for 5 minutes, standing vitals after upright for 1 minute, JVP height from sternal angle with torso at 45 degrees.[9,10] Hematologic and biochemical data included hematocrit, serum urea, creatinine, electrolytes, and urine specific gravity in all patients. Serum phosphate and ionized calcium were measured in approximately 30 randomly chosen patients from each group.

Patient Acceptance/Tolerability

On the morning of colonoscopy and prior to the procedure patients completed a multiple-choice questionnaire designed to assess their tolerance of the bowel preparation. The questionnaire was similar to that used by previous investigators[11] but also included questions pertaining to the estimated amount and perception of the ingested fluid volume. Thus, patients were asked to estimate the number of 8-ounce glasses of fluid consumed during the preparation period and to assess whether the prescribed fluid volume was too small, acceptable or too large.

Endoscopic Evaluation

Quality of colonic cleansing was assessed using a previously validated questionnaire[11] that was completed by one of 5 attending gastroenterologists in the outpatient endoscopy unit. Endoscopists were instructed not to ask patients about the details of the bowel preparation. They rated the quality of visualization as either excellent, good, fair, poor or unacceptable. To assess whether endoscopists were blinded to the treatment group, they also selected a color, from a list of seven choices, which most closely approximated that of the luminal fluid observed during the procedure.

Statistical Analysis

Published observations[1,7] indicate that approximately 20% of patients who receive oral NaP-based colonic purgation for colonoscopy experience orthostatic changes in pulse and systemic arterial blood pressure. Based on this baseline estimate, a sample size of 76 patients in each arm was calculated in order to detect at least a 75% reduction in the incidence of orthostasis, with 80% power and a two-sided $\alpha$ of 0.05. Paired continuous variables were analyzed using the Wilcoxon signed rank test followed by the Mann Whitney U test to compare differences between groups. Categorical variables were assessed using the chi-square test or Fisher's exact test. Data are expressed as means±standard deviation (SD). A two-sided p value less than 0.05 was considered statistically significant. Statistical analysis was performed using GRAPHPAD INSTAT™ software (San Diego, Calif.).

TABLE 1

Demographic and baseline clinical data

| | Clear Fluids (CF) | Gatorade (G) |
|---|---|---|
| N | 81 | 87 |
| Age (mean ± SD) | 54 ± 13 | 53 ± 13 |
| Males/Females | 42/39 | 39/48 |
| Adenoma Screen/Survey | 60 (74%) | 52 (60%) |
| Cardiovascular disease | 21 (26%) | 17 (20%) |
| Diabetes mellitus | 2 (3%) | 3 (4%) |
| Opiate/anticholinergic Rx | 8 (10%) | 5 (6%) |
| Diuretic Rx | 6 (7%) | 7 (8%) |
| Beta-blocker Rx | 4 (5%) | 2 (2%) |

TABLE 2

Clinical hemodynamic data

| | CF (mean ± SD) | G (mean ± SD) | p value |
|---|---|---|---|
| ΔWeight (kg) | −3.12 ± 2.06 | −2.69 ± 1.77 | 0.0677[υ] |
| Δ JVP (cm) | −0.71 ± 1.81 | 0.01 ± 1.86 | 0.0172[υ] |
| $\Delta_A$ HR | 6.66 ± 8.43 | 3.87 ± 8.67 | 0.0203[υ] |
| $\Delta_A$ SBP | −6.73 ± 9.08 | −4.41 ± 9.34 | 0.1334[υ] |
| $\Delta_A$ HR, SBP ≧ 10* | 53 (65%) | 37 (43%) | 0.0051[f] |
| $\Delta_A$ HR, SBP ≧ 15* | 28 (35%) | 19 (22%) | 0.0862[f] |
| $\Delta_A$ HR, SBP ≧ 20* | 13 (16%) | 10 (12%) | 0.5020[f] |

CF, clear fluids;
G, Gatorade;
Δ, difference;
JVP, jugular venous pressure;
HR, heart rate;
SBP, systolic blood pressure;
*values represent number (%) of subjects with indicated changes in HR and/or SBP;
[υ]Mann-Whitney U test;
[f]Fisher's exact test.

TABLE 3

Hematologic and biochemical data

| | CF (mean ± SD) | G (mean ± SD) | p value[υ] |
|---|---|---|---|
| Δhematocrit (%) | 0.194 ± 1.935 | −0.589 ± 2.038 | 0.0117 |
| Δserum Na$^+$(mmol/L) | 2.18 ± 2.81 | 1.67 ± 2.95 | 0.1440 |
| Δserum K$^+$ (mmol/L) | −0.61 ± 0.37 | −0.61 ± 0.43 | 0.7088 |
| Δserum PO$_4$ (mmol/L) | 0.39 ± 0.30 | 0.35 ± 0.43 | 0.4814 |
| Δserum Ca$^{++}$ (mmol/L) | −0.075 ± 0.050 | −0.076 ± 0.044 | 0.8908 |

TABLE 3-continued

Hematologic and biochemical data

| | CF (mean ± SD) | G (mean ± SD) | p value[v] |
|---|---|---|---|
| Δserum urea (mmol/L) | −1.00 ± 1.16 | −1.74 ± 1.45 | <0.0001 |
| Δserum Cr (μmol/L) | 1.58 ± 8.65 | −2.40 ± 9.33 | 0.0127 |
| Δurine SG | 0.0085 ± 0.0109 | 0.0014 ± 0.0107 | 0.0001 |

CF, clear fluids;
G, Gatorade;
Δ, difference;
Na+, sodium;
K+, potassium, PO4, phosphate;
Ca++, ionized calcium;
Cr, creatinine;
SG, specific gravity;
[v]Mann-Whitney U test.

TABLE 4

Symptom profiles of Clear Fluid/Gatorade subjects*

| Symptom | None | Mild | Moderate | Severe | In-tolerable | p value |
|---|---|---|---|---|---|---|
| Bloating | 52/58 | 18/17 | 10/10 | 1/1 | 0/0 | 0.6735[x] |
| Dizzy | 61/69 | 14/18 | 6/10 | 1/0 | 0/0 | 0.6061[x] |
| Nausea | 38/39 | 18/23 | 23/15 | 3/10 | 0/0 | 0.7917[x] |
| Vomiting | 70/75 | 2/4 | 6/4 | 4/3 | 0/1 | 0.7319[x] |
| Pain | 57/56 | 16/18 | 5/11 | 4/2 | 0/0 | 0.3577[x] |
| Poor sleep | 53/55 | 15/17 | 10/11 | 4/4 | 0/0 | 0.9102[x] |
| Taste | 5/8 | 41/37 | 32/27 | 4/15 | — | 0.2673[x] |
| Tolerability | 35/34 | 17/18 | 23/15 | 2/6 | 4/13 | 0.1976[x] |
| Complete | Yes 75/65 | No 6/21 | — | — | — | 0.0031[f] |
| Other prep | Yes 41/43 | No 41/44 | — | — | — | 0.9405[f] |
| Refuse | Yes 9/12 | No 73/75 | — | — | — | 0.5789[f] |

*Values in each cell denote number of CF/G subjects; small numbers of subjects in certain categories were pooled as necessary to satisfy criteria for statistical analysis;
[x]chi-square test for trend;
[f]Fisher's exact test.

Results

Between 1st March and 24th May, 2001, one hundred and seventy-one consecutive outpatients scheduled to undergo NaP for colonoscopy were randomized to either regular clear fluids or oral rehydration solution during NaP preparation for colonoscopy (Table 1). Six patients declined entry into the study and 10 patients were excluded because of contraindications to NaP. Of the 171 patients randomized, 3 failed to show or cancelled the procedure, leaving 168 patients who completed the study. There were no significant differences in demographic, comorbid or medication profiles between the two groups. The most common indication for colonoscopy (approximately two-thirds of patients) was screening or surveillance for neoplastic polyps.

Clinical Hemodynamic Data

Compared to baseline values obtained at the initial clinic visit (Table 2), mean weight loss in CF subjects was nearly 15% greater than in G subjects (p=0.0677). JVP fell significantly in the CF subjects compared to G subjects in whom the mean change in JVP was negligible (p=0.0172). Although both CF and G groups experienced modest mean changes in orthostatic vitals, these changes were more pronounced in CF than in G subjects; the mean orthostatic increase in pulse was 2-fold greater in CF subjects compared to G subjects (p=0.0203); similarly, the mean fall in systolic blood pressure (SBP) in the CF group was approximately 1.5-fold greater than in G subjects (p=0.1334). A significantly greater proportion of CF subjects (65%) vs. G subjects (43%) experienced a fall in SBP and/or a rise in pulse rate of ≧10 points (p=0.0051); similarly, 35% of CF subjects vs. 22% of G subjects experienced a change in orthostatic vitals of at least 15 points (p=0.0862). The greatest orthostatic increases in pulse were 30 beats per minute in the CF group and 28 in the G group; for orthostatic SBP the maximum changes were −24 mm Hg in the CF group and −28 mm Hg in the G group.

Hematologic and Biochemical Data

Changes in hematology and biochemistry (Table 3) also suggested a greater degree of plasma volume contraction in CF subjects than in the G group. Urine specific gravity increased by approximately 6-fold more in the CF group compared to the G group (p=0.0001), in keeping with significantly greater urinary concentration in the former group. Hematocrit increased by a small degree in CF subjects but decreased by three times as much in G subjects (p=0.0117), in keeping with relative hemoconcentration in the CF group. Compared to baseline, serum creatinine increased by approximately 2% in CF subjects but decreased by 3% in G subjects (p=0.0127). Serum urea decreased in both groups but the mean decline was nearly 2-fold greater in G than in CF subjects (p<0.0001). There were no significant differences observed in any of the other biochemical variables measured, including serum electrolytes. Although both groups exhibited similar mean decreases in serum calcium levels (approximately 6% from baseline), the lowest individual post-NaP calcium levels occurred in the CF group (e.g. 1.05, 1.08 mmol/L; normal range 1.19 to 1.31 mmol/L).

Symptoms/Tolerability

CF and G subjects had similar symptom profiles during the preparation period (Table 4). Overall tolerability of the two preparation protocols was similar, with approximately two-thirds of both CF subjects and G subjects finding the respective preparation easy or only slightly difficult to tolerate (p=0.1976). A greater proportion of G subjects reported not being able to complete the prescribed preparation (25% vs. 7%, p=0.0031) but there were no differences in the proportions of subjects who would have preferred a different preparation (approximately 50% of both groups, p=0.9405) or who stated that they would refuse the same preparation in the future (11% of CF subjects vs. 14% of G subjects, p=0.5789). The reported fluid volume ingested during the preparation period was slightly greater in the G subjects than in the CF group (difference of 0.43L, p=0.0002) and half of the G subjects felt the prescribed fluid volume was too large compared to only 10% of CF subjects (p<0.0001).

Quality of Bowel Preparation

There were no significant differences in the color of luminal fluid noted between groups (p=0.6426) at the time of colonoscopy, with green the color noted most frequently (57% of CF subjects and 48% of G subjects). FIG. 1 shows the quality of colonic preparation in CF (open bars) and G subjects (solid bars). Due to small numbers, subjects with "Unacceptable" preparations were pooled with subjects in the "Poor" category. The value with an "*" is the chi-square test, for trend.

As shown in FIG. 1, the quality of the bowel preparation was significantly better in the G group than in the CF group. Seventy-one % of G subjects had a good or excellent preparation compared to 56% of CF subjects. Similarly, only 3% of G subjects had a poor or unacceptable preparation vs. 12% of CF subjects (p=0.0056).

REFERENCES

1. Vanner S J, MacDonald P H, Paterson W G, Prentice R S A, Da Costa L R, Beck I T. A randomized prospective trial comparing oral sodium phosphate with standard polyethylene glycol-based lavage solution (Golytely) in the preparation of patients for colonoscopy. Am J Gastroenterol 1990; 85:422-7.

2. Marshall J B, Pineda J J, Barthel J S, King P D. Prospective, randomized trial comparing sodium phosphate solution with polyethylene glycol-electrolyte lavage for colonoscopy preparation. Gastrointest Endosc 1993; 39:631-4.

3. Kolts B E, Lyles W E, Achem S R, Burton L, Geller A J, MacMath T. A comparison of the effectiveness and patient tolerance of oral sodium phosphate, castor oil, and standard electrolyte lavage for colonoscopy or sigmoidoscopy preparation. Am J Gastroenterol 1993;88:1218-23.

4. Cohen S M, Wexner S D, Binderow S R, Nogueras J J, Daniel N, Ehrenpreis E D, et al. Prospective, randomized, endoscopic-blinded trial comparing precolonoscopy bowel cleansing methods. Dis Colon Rectum 1994;37:689-96.

5. Chan A, Depew W, Vanner S. Use of oral sodium phosphate colonic lavage solution by Canadian colonoscopists: pitfalls and complications. Can J Gastroenterol 1997; 11:334-8.

6. Brunton L. Laxatives and cathartics. In: Gilman A, Goodman A, Rall T W, et al., eds. The pharmacological basis of therapeutics, $7^{th}$ ed. New York: Macmillan, 1985:934.

7. Huynh T, Vanner S, Paterson W. Safety profile of 5-h oral sodium phosphate regimen for colonoscopy cleansing: lack of clinically significant hypocalcemia or hypovolemia. Am J Gastroenterol 1995;90:104-7.

8. Avery M E, Snyder J D. Oral therapy for acute diarrhea: The underused simple solution. N Engl J Med 1990:13:891-4.

9. Williams T, Knapp R. The clinical use of orthostatic vital signs. In: Roberts J R, Hedges J R, eds. Clinical procedures in emergency. Philadelphia: W B Saunders, 1985.

10. Mcgee S R. Physical examination of venous pressure: a critical review. Am Heart H. 1998;136:10-8.

11. Aronchick C A, Lipshutz W H, Wright S H, Dufrayne F, Bergman G. A novel tableted purgative for colonoscopic preparation: efficacy and safety comparisons with Colyte and Fleet Phospho-Soda. Gastrointest Endosc 2000;52:346-52.

12. Johnson D R, Douglas D, Hauswald M, Tandberg D. Dehydration and orthostatic vital signs in women with hyperemesis gravidarum. Acad Emerg Med 1995;2:692-7.

13. Kuchel G A, Avorn J, Reed M J, Fields D. Cardiovascular responses to phlebotomy and sitting in middle-aged and elderly subjects. Arch Int Med 1992;152:366-70.

14. Klein S, Fleming C R. Enteral and parenteral nutrition. In: Feldman M, Scharschmidt B F, Sleisenger M H, eds. Sleisenger and Fordtran's gastrointestinal and liver disease. Philadelphia: W B Saunders, 1998:254-77.

15. Greenleaf J E, Jackson C G, Geelen G, Keil L C, Hinghofer-Szalkay H, Whittam J H. Plasma volume expansion with oral fluids in hypohydrated men at rest and during exercise. Aviat Space Environ Med 1998;69:837-44.

16. Maughan R J, Owen J H, Shirreffs S M, Leiper J B. Post-exercise rehydration in man: effects of electrolyte addition to ingested fluids. Eur J Appl Physiol Occup Physiol 1994;69:209-25.

17. Shaoul R, Wolff R, Seligmann J, Tal Y, Jaffe M. Symptoms of hyperphosphatemia, hypocalcemia, and hypomagnesemia in an adolescent after the oral administration of sodium phosphate in preparation for a colonoscopy. Gastrointest Endosc 2001;53:650-2.

18. Barclay R L, Depew W T, Vanner S J, Carbohydrate-electrolyte rehydration protects against intravascular volume contraction during colonic cleansing with orally administered sodium phosphate. Gastrointest Endosc 2002;56:633-8.

The invention claimed is:

1. A method of colonic cleansing in patients, comprising:
orally administering an osmotic colonic evacuant, wherein said evacuant comprises sodium phosphate; and
orally administering an oral rehydration solution;
wherein the oral rehydration solution comprises
(a) 5-7% (w/v) sugar mixture comprising sucrose, glucose and fructose,
(b) 10-200 mmol/L sodium containing salt, and
(c) water,
the patients maintain a fluid only diet for 24 hours prior to a colonoscopy, and at least 50% of all fluids orally administered from 4 hours before to 24 hours after orally administering the osmotic colonic evacuant are the oral rehydration solution.

2. The method of claim 1, wherein the orally administering of the osmotic colonic evacuant is after the orally administering of the oral rehydration solution.

3. The method of claim 1, wherein the oral rehydration solution further comprises a flavoring agent.

4. The method of claim 1, wherein the oral rehydration solution further comprises a coloring agent.

5. The method of claim 1, wherein the salt further comprises potassium.

6. The method of claim 1, wherein the oral rehydration solution further comprises a flavoring agent and potassium.

7. The method of claim 1, wherein the osmotic colonic evacuant is administered at a first time during a first day and a second time during the first day, and the administering of the oral rehydration solution is carried out from the first time to the morning of the next day.

8. The method of claim 7, wherein the first time is 5 PM.

9. The method of claim 7, wherein the second time is 10 PM.

10. The method of claim 7, wherein the colonoscopy on the patients is carried out during the next day.

11. The method of claim 1, wherein the administering of the oral rehydration solution is carried out from 5 PM during a day to the morning of the next day.

12. The method of claim 11, wherein the colonoscopy on the patients is carried out during the next day.

13. The method of claim 1, wherein the oral rehydration solution has a concentration of said salt of 10-30 mmol/L.

14. The method of claim 13, wherein the salt further comprises potassium.

15. The method of claim 1, wherein at least 90% of all fluids orally administered from 4 hours before to 24 hours after orally administering the osmotic colonic evacuant are the oral rehydration solution.

16. The method of claim 1, wherein the patients have statistically significant superior bowel colonic cleansing, as compared to other patients who consumed only clear fluids, and
the clear fluids comprise water, juices and/or carbonated beverages, and do not comprise commercial sports drinks.

17. The method of claim 1, wherein the oral rehydration solution consists essentially of 6% (w/v) said sugar mixture, 20 mmol/L sodium, 3 mmol/L potassium and water.

* * * * *